(12) United States Patent
Kubein-Meesenburg et al.

(10) Patent No.: US 6,443,994 B1
(45) Date of Patent: Sep. 3, 2002

(54) EXOPROSTHESIS FOR THE HUMAN KNEE-JOINT

(75) Inventors: Dietmar Kubein-Meesenburg, Kreiensen; Hans Naegerl, Gleichen, both of (DE)

(73) Assignee: HJS Gelenk-System GmbH, Munich (DE)

( * ) Notice: Subject to any disclaimer, the term of this patent is extended or adjusted under 35 U.S.C. 154(b) by 0 days.

(21) Appl. No.: 09/554,891
(22) PCT Filed: Nov. 17, 1998
(86) PCT No.: PCT/DE98/03390
§ 371 (c)(1), (2), (4) Date: May 22, 2000
(87) PCT Pub. No.: WO99/26564
PCT Pub. Date: Jun. 3, 1999

(30) Foreign Application Priority Data

Nov. 21, 1997 (DE) .......................... 197 51 758

(51) Int. Cl.⁷ .................................................. A61F 2/62
(52) U.S. Cl. ............................................ 623/39; 602/16
(58) Field of Search ............................. 623/43, 44, 45, 623/16, 39; 602/26

(56) References Cited

U.S. PATENT DOCUMENTS

| | | | | |
|---|---|---|---|---|
| 3,863,274 A | * | 2/1975 | Glabiszewski | 623/44 |
| 4,738,252 A | * | 4/1988 | Friddle et al. | 403/97 |
| 5,062,858 A | * | 11/1991 | Broeck et al. | 623/43 |
| 5,419,754 A | * | 5/1995 | Hutchins | 602/16 |
| 5,443,444 A | * | 8/1995 | Pruyssers | 602/26 |
| 5,860,943 A | * | 1/1999 | Bloedau et al. | 16/354 |
| 6,203,511 B1 | * | 3/2001 | Johnson et al. | 602/16 |

* cited by examiner

Primary Examiner—Paul B. Prebilic
Assistant Examiner—William H. Matthews
(74) Attorney, Agent, or Firm—Crowell & Moring LLP

(57) ABSTRACT

An exoprosthesis/orthosis for the human knee-joint comprised of an upper leg part (1) which can be connected to the human upper leg, and a lower leg part (2) which can be connected to the human lower leg. Both leg parts (1, 2) are connected at least via a joint which constructs a joint with two joint axes ($M_U$, $M_O$), i.e. a so-called dimeric joint chain, which are connected such that they carry out a forced movement. A polode (movement or rest polode) is assigned to each respective leg part (1, 2) with regard to the momentary joint axis of said leg parts, whereby curved teeth (5, 7) are constructed on the upper leg part (1) and on the lower leg part (2). The teeth interact similar to sprocket gearing in the movement functional area of the joint (3), whereby the curved teeth coincide with the polodes (t, f) of both leg parts (1, 2) in the movement functional area.

4 Claims, 3 Drawing Sheets

EXOPROSTHESIS FOR THE HUMAN KNEE-JOINT

Figure 1:
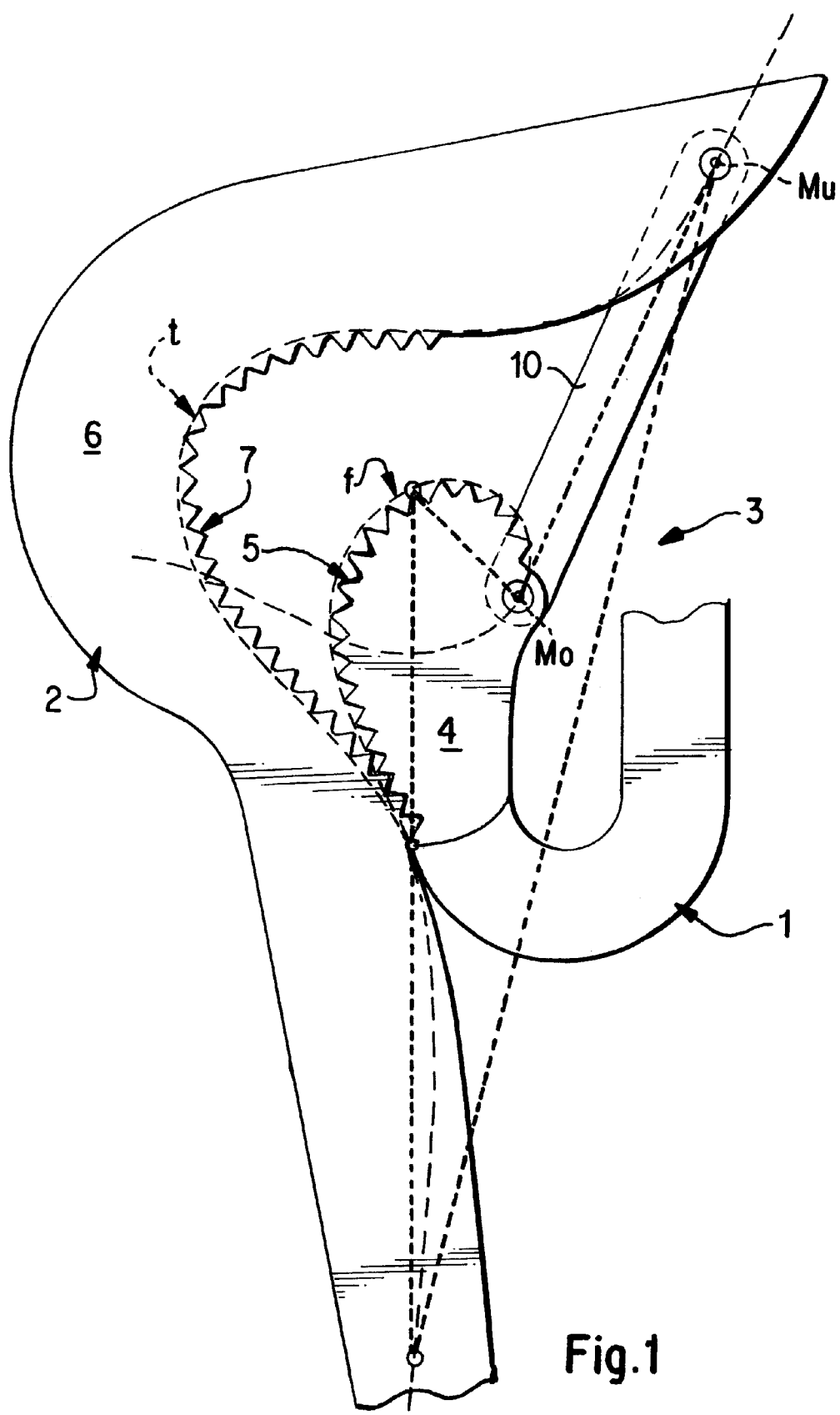

The invention presented relates to an exoprosthesis/orthosis for the human knee-joint comprising an upper leg part which can be connected to the human upper leg as well as a lower leg part which can either be connected to the human lower leg or replace it, where both parts are connected to each other via at least one joint which constructs a joint with two joint axes, i.e. a dimeric joint chain, and carries out a constrained movement, such that both leg parts, with regard to their momentary joint axis, respectively have a corresponding curve path (movement or rest curve path).

An exoprosthesis for the human knee-joint is known from DE-OS 43 09 577. In this joint, the lower leg part and the upper leg part are connected by a four-joint arrangement formed by two parallel-arranged partial joints, namely a medial joint and a lateral joint, which each have the joint geometry of a joint chain with two joint axes (dimeric joint chain). The joint geometry of the medial joint is designed as an overlapping dimeric joint chain in which the joint axis of the lower leg part is displaced towards the direction of the upper leg part with respect to the joint axis of the upper leg part, and the joint geometry of the lateral joint is designed as an extended dimeric chain. Here, the joint axis of the lower leg part is displaced towards the direction of the lower leg with respect to the joint axis of the upper leg part. In each case, both the joint axes of the lateral joint and of the medial joint are connected to each other in an articulated manner by means of a coupling. With this four-joint design, a fixed, predetermined constrained movement of the lower leg with respect to the femur results, or vice versa. In the case of such a constrained movement of the lower leg part with respect to the upper leg part or vice versa, each respective joint part has a specific corresponding rest or movement curve path. The curve paths (rest curve path-movement curve path) are the curve paths on which lie the respective instantaneous centers of motion resulting from a continuous motion. The calculations for obtaining these curve paths are common knowledge.

It is the object of this invention, based on the known exoprosthesis/orthosis, to replace this with a simpler and more space-efficient construction.

This object is solved according to the invention by designing a curving toothed gearing section on both the upper leg joint section and the lower leg joint section whose teeth engage in the movement functional area of the joint, whereby the curved path of the gearing coincides with the curve paths of both joint sections in the movement functional area. Here, according to the invention, a four-joint arrangement is not imitated directly, but rather indirectly, as the rest curve path curve and movement curve path curve of the joint are approximated with gearing sections, which then, depending on their particular arrangement, engage with each other and thereby enable a counter-rotational encounter of the curve paths. The rest curve path in the reference system of the femur should be open ended at the bottom, and the instantaneous center of motion should move in a forwards direction from the extension to the bend. If the gearing path is matched to the respective curve path, a cam mechanism results, and the characteristic mechanism of a natural knee is nearly attained. The curve pair of gearings predetermines a constrained movement which rules out any slippage. In order to prevent the curved pair of gearings from becoming disengaged, the upper leg part and the lower leg part must be connected by a second joint connection (dimeric joint chain), comprising the joint axis found in the upper leg part, the joint axis found in the lower leg part, and a coupling located between these. In accordance with the invention, it can be advantageous if the curve paths are approximated by semi-circles whose middle points are used as joint axes. The joint section forming the femur (upper leg joint section) can thus, for example, be provided with an outer gearing, and the joint section forming the tibia (lower leg joint section) with an interior gearing, wherein the two gearings then engage with each other in the joint functional region. Design as a toothed gear segment enables a simple mode of production. If the middle points of the gears (approximate curve paths) or the gears' axes of rotation are connected to each other via a coupling, the constrained motion of the system is guaranteed when forces are applied, that is, the geared joint sections are prevented from separating from each other since the coupling adds a load transmitting dimeric chain. In place of a separate coupling, however, a joint sheath can be provided, where the sheath sides serve at the same time as a load transmitting coupling.

Designing the invention as a geared joint results in a very compact version of the exoprosthesis which can also be produced economically.

The invention is explained in further detail with the aid of the exemplary embodiments shown in the accompanying drawings. Shown are:

FIG. 1 a lateral view of an inventive exoprosthesis/orthosis

Figure 3:
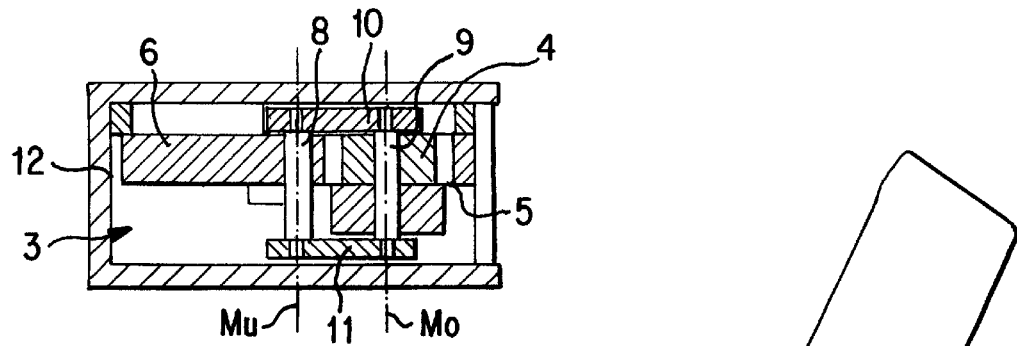
Figure 2:
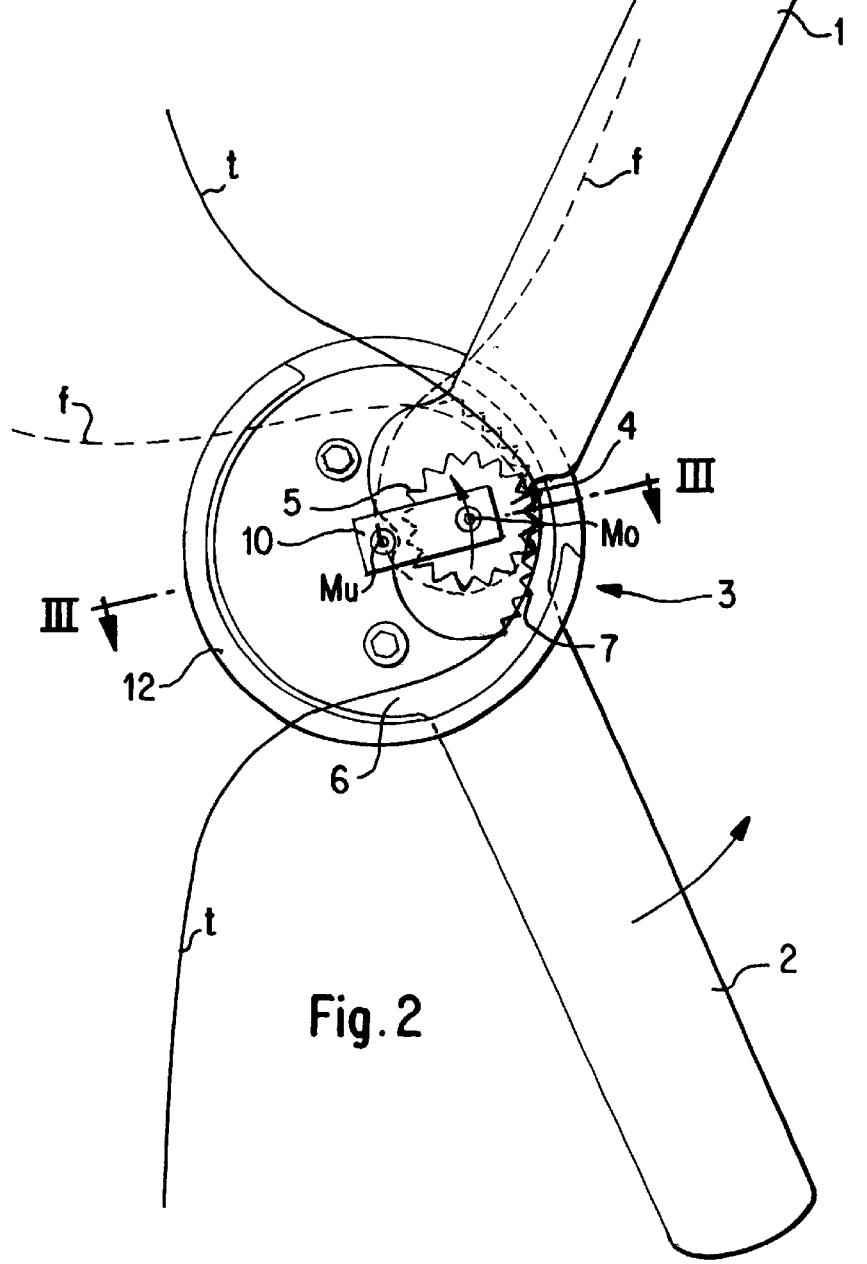

FIG. 2 a lateral view of another embodiment of an inventive exoprosthesis/orthosis FIG. 3 a cross section marked by the line III—III in FIG. 2.

Figure 4:
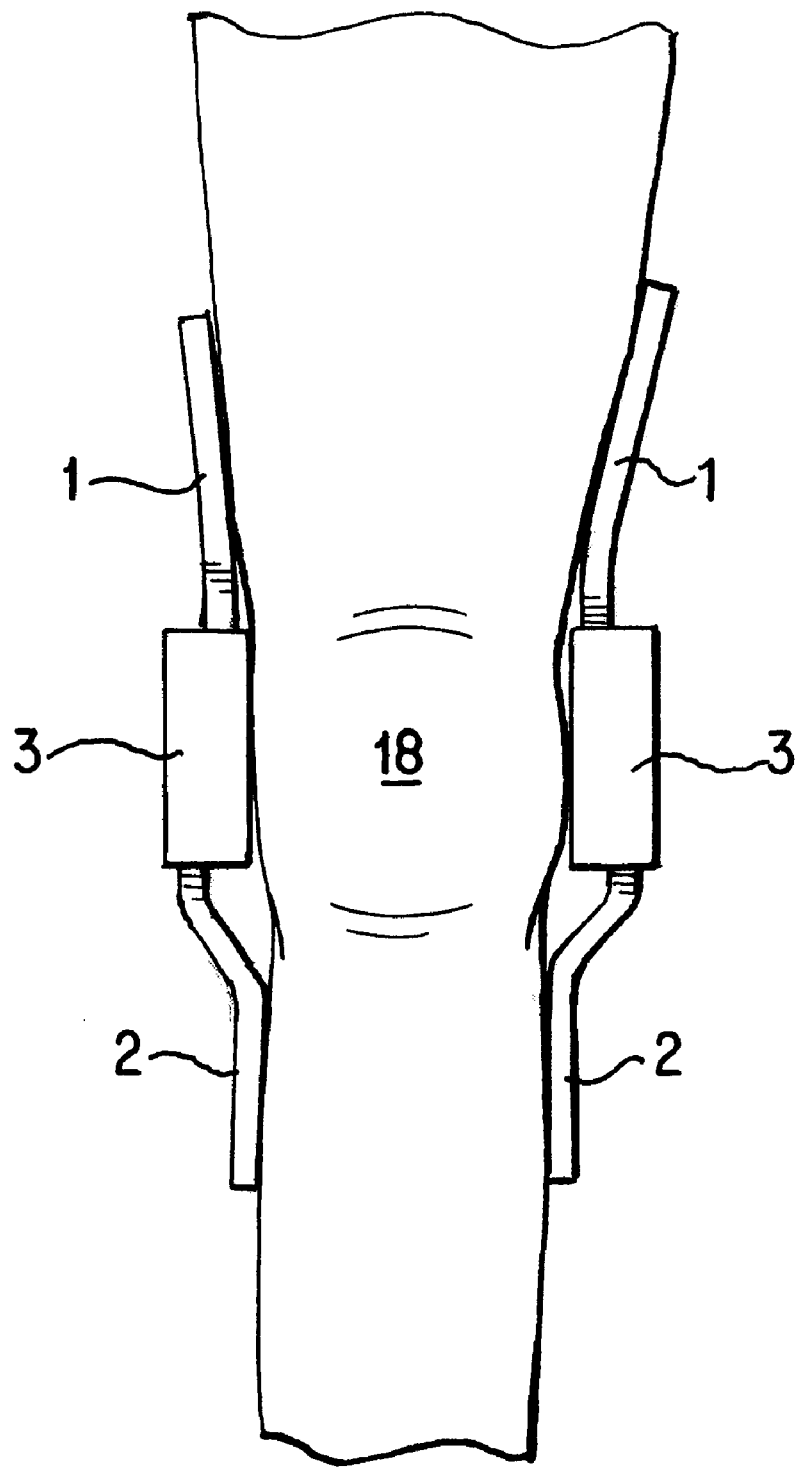

FIG. 4 a view of a human knee with the inventive exoprosthesis affixed to it

In FIGS. 1 through 4, the same numbers are used to refer to the same parts.

As can be seen in FIG. 1, the inventive exoprosthesis comprises an upper leg part 1 and a lower leg part 2. Both these parts 1 and 2 are functionally connected to the upper leg or lower leg of the human leg, respectively. The lower part 2 can also replace the lower leg of the human leg. The lower leg part 2 and the upper leg part 1 are connected to each other via a joint 3. Here, it is a joint which is designed as a so-called dimeric joint chain. This joint has two joint axes, the joint axis $M_u$ and the joint axis $M_o$. The joint axis $M_u$ belongs to the lower leg part, and the joint axis $M_o$ belongs to the upper leg part. Within joint 3, the upper leg part 1 has a joint extension 4. This joint extension 4 has an exterior gearing 5. The lower leg part 2 has a joint section 6, on which is located an interior gearing 7. The exterior gearing 5 follows a curved path corresponding to the path of the pole curve f of the upper leg in the functional region of joint 3. The interior gearing 7 follows a curved path corresponding to the path of the pole curve t located in the lower leg. The paths of gearing sections 5 and 7 can be matched exactly to the paths of the respective pole curves, such that a cam mechanism is then formed. Thus, for each of the leg parts 1 and 2, a curve path is predetermined (a movement or rest curve path depending on the system of reference) which corresponds to the physiological movement of the human knee. In a straight position, the gearing curvature t of the tibial joint section 2 runs from a caudal direction to a cranial direction with an outward curve to the posterior (FIG. 1). The gearing curvature f located in the upper leg part 1 has a convex curvature when seen from above and from the posterior. Since the paired curvatures of the gearing sections (comprising the gearing curvature t belonging to the lower leg 2 and the gearing curvature f belonging to the upper leg 1) only remain in contact when subjected to tensile forces between the upper leg part and lower leg part, a second articulated connection is provided in the joint (a dimeric joint chain), comprising an axis $M_o$ located in the upper leg part 1 and an axis $M_u$ located in the lower leg part 2 and their coupling 10. This connection ensures the guiding function of the paired curvatures of the gearing even under compressive forces. The axis $M_o$ located in the upper leg part 1 intersects the gearing curvature f belonging to the upper leg part 1; the axis $M_u$ located in the lower leg part 2 intersects the gearing curvature t belonging to the lower leg part 2. The positions of both of the axes are selected such that the distance between them remains constant and that the constrained guidance is thus not influenced by the paired curvatures of the gearing.

In the exemplary embodiment in accordance with FIG. 2, the gearing sections 5, 7 form part of a semi-circle, where the semi-circles each depict part of a circle around the appropriate joint axes $M_o$ and $M_u$. Here, the circles in the joint functional region are practically equivalent to the path of the respective pole curves. Bearing axles 8, 9 run through joint axes $M_o$ and $M_u$, as can particularly be seen in FIG. 3. Both bearing axles 8, 9 are connected to each other in an articulated manner via coupling 10, 11. Yet another load transmitting dimeric chain is formed within joint 3 by this coupling 10, 11, whereby a constrained movement of the system is guaranteed when forces are applied.

The coupling pieces 10, 11 prevent separation of the gearing regions during the joint's operation. The gearing sections 5, 7 operate in relation to one another such that both gearing sections engage each other on their sections 4, 6 when the leg parts 1, 2 move relative to each other. The joint sections 4, 6 are located within a housing 12. The bearing axle 8 is inserted within the joint section 6 and the bearing axle 9 is inserted within the joint section 4.

The inventive exoprosthesis can be produced from synthetic material or metal or a combination of metal and synthetic material.

As can be seen in FIG. 4, the inventive exoprosthesis is attached to the human knee 18 either on one or both sides, i.e. laterally and/or medially.

The invention presented is not restricted to the exemplary embodiments shown, but rather embraces all means which, in the sense of the invention, operate similarly to the lower leg with regard to structure and motion. Such means encompass, for example, two pins which are stationarily attached to the lower leg (or in the upper leg part) and which engage in curved grooves and are guided by them, where these grooves are cut in a metal piece (or other work piece) which is connected to be stationary to the upper leg part (or lower leg part). The guiding grooves are designed such that, on the whole, the structure of relative movement between upper leg part and lower leg part is achieved as it can be achieved using the above paired gearing curvatures.

What is claimed is:

1. Exoprosthesis for a human knee-joint, comprising an upper leg part which can be connected to a human upper leg and a lower leg part which can be connected to a human lower leg, wherein both leg parts are connected via at least one joint which constructs a joint with two joint momentary axes which are connected so as to carry out a constrained movement, wherein both leg parts, with regard to their momentary joint axes, each respectively has a corresponding curve path on which lies instantaneous centers of motion resulting from a continuous motion and, on both the upper leg part and the lower leg part, curving toothed gearing sections are located which act on each other in an articulated manner in a movement functional area of the joint, wherein a path of the gearing curvatures coincides with the curve paths of both leg parts in the movement functional area, and wherein, when in a straight position, a gearing curvature of the lower leg part runs as interior gearing with an outward curve towards the posterior, and a gearing curvature of the upper leg part runs as exterior gearing with a convex curvature.

2. Exoprosthesis in accordance with claim 1, wherein the interior gearing and the exterior gearing lie on respective circles around the joint axes.

3. Exoprosthesis in accordance with claim 1, wherein the leg parts have joint sections which are connected in an articulated manner via at least one coupling between joint axes of the joint sections.

4. Exoprosthesis in accordance with claim 3, wherein said at least one coupling includes first and second medial or lateral coupling pieces located in parallel planes.

* * * * *